(12) United States Patent
Shimizu et al.

(10) Patent No.: US 7,927,842 B2
(45) Date of Patent: Apr. 19, 2011

(54) METHOD OF PREPARING 2-DEOXYRIBOSE 5-PHOSPHATE

(75) Inventors: Sakayu Shimizu, Kyoto (JP); Jun Ogawa, Kyoto (JP)

(73) Assignees: Yuki Gosei Kogyo Co. Ltd., Tokyo (JP); Novartis AG, Basel (CH)

( * ) Notice: Subject to any disclaimer, the term of this patent is extended or adjusted under 35 U.S.C. 154(b) by 827 days.

(21) Appl. No.: 11/878,553

(22) Filed: Jul. 25, 2007

(65) Prior Publication Data

US 2007/0298467 A1 Dec. 27, 2007

Related U.S. Application Data

(60) Division of application No. 10/652,252, filed on Sep. 2, 2003, now Pat. No. 7,270,992, which is a continuation of application No. PCT/JP02/01747, filed on Feb. 26, 2002.

(30) Foreign Application Priority Data

Mar. 2, 2001 (JP) ................. 2001-058902

(51) Int. Cl.
C12P 19/02 (2006.01)
(52) U.S. Cl. ...................... 435/105; 435/252.1; 435/131

(58) Field of Classification Search ........................ None
See application file for complete search history.

(56) References Cited

OTHER PUBLICATIONS

Hall et al., Biochemistry, vol. 14, 1975, pp. 4348-4352.*
Gijsen et al., Chem. Rev. 1996, 96, 443-473.*
Wong et al., J. Am. Chem. Soc., vol. 117, pp. 3333-3339 (1995).
Chen et al., J. Am. Chem. Soc., vol. 114, pp. 741-748 (1992).
Barbas et al., J. Am. Chem. Soc., vol. 112, pp. 2013-2014 (1990).
N. Itoh et al., Appl. Microbiol. Biotechnol, vol. 51, pp. 193-200, 1999.

* cited by examiner

*Primary Examiner* — Irene Marx
(74) *Attorney, Agent, or Firm* — Birch, Stewart, Kolasch & Birch, LLP

(57) ABSTRACT

The present invention discloses a method of preparing 2-deoxyribose 5-phosphate by reacting glyceraldehyde 3-phosphate and acetaldehyde in the presence of either a microorganism itself which contains 2-deoxyribose-5-phosphate aldolase but substantially no phosphatase or the enzyme derived from the microorganism. The present invention also discloses a method of preparing 2-deoxyribose 5-phosphate by reacting dihydroxyacetone phosphate and acetaldehyde in the presence of either a microorganism itself which contains 2-deoxyribose-5-phosphate aldolase and triose-phosphate isomerase but substantially no phosphatase or the enzymes derived from the microorganism.

5 Claims, 5 Drawing Sheets

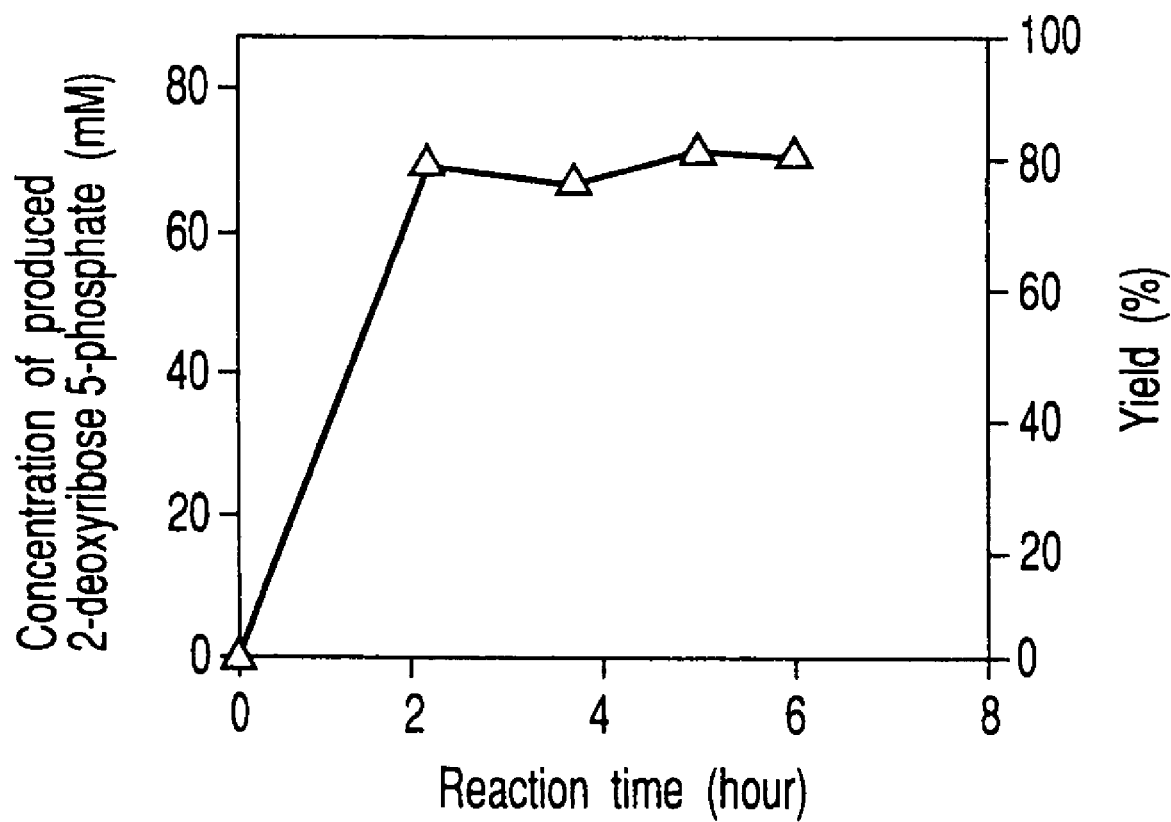
F I G. 9

METHOD OF PREPARING 2-DEOXYRIBOSE 5-PHOSPHATE

CROSS-REFERENCE TO RELATED APPLICATIONS

This application is a Divisional of application Ser. No. 10/652,252 filed on Sep. 2, 2003, now U.S. Pat. No. 7,270,992 which is a Continuation of PCT Application No. PCT/JP02/01747, filed Feb. 26, 2002. PCT/JP02/01747 claims the benefit of priority of Japanese Patent Application No. 2001-058902, filed Mar. 2, 2001. The entire contents of these applications are incorporated herein by reference.

TECHNICAL FIELD

The present invention relates to a method of preparing 2-deoxyribose 5-phosphate stably at a high yield by using a microorganism itself or an enzyme derived from the microorganism. The present invention also relates to a microorganism capable of producing an enzyme which can be utilized for the preparation of 2-deoxyribose 5-phosphate. 2-deoxyribose 5-phosphate is used as a starting material in the biochemical synthesis of deoxynucleosides. Further, by dephosphorylating 2-deoxyribose 5-phosphate, 2-deoxyribose can be obtained. 2-deoxyribose is useful as a starting material in the chemical synthesis of nucleosides.

BACKGROUND ART 2-deoxyribose 5-phosphate has conventionally been prepared by hydrolyzing DNA with an enzyme or chemically phosphorylating 2-deoxyribose. However, the former method has a problem that DNA as the raw material is expensive and a number of separation/purification processes are required. The latter method also has a problem that regioselective phosphorylation of 2-deoxyribose is difficult. Thus, 2-deoxyribose 5-phosphate cannot be prepared inexpensively by either of the above-mentioned two methods.

In vivo, it has been known that 2-deoxyribose 5-phosphate is produced from glyceraldehyde 3-phosphate and acetaldehyde, by the catalytic action of 2-deoxyribose-5-phosphate aldolase (deoxyribose-phosphate aldolase EC 4.1.2.4). However, the preparation of 2-deoxyribose 5-phosphate according to the aforementioned reaction has a problem that chemical synthesis of glyceraldehyde 3-phosphate as one substrate is not easy and glyceraldehyde as the other substrate is unstable and apt to be isomerized to dihydroxyacetone that is a more stable isomer.

It is also known that glyceraldehyde 3-phosphate is produced in vivo, as a result of an isomerization reaction in which dihydroxyacetone phosphate is isomerized by triose-phosphate isomerase (EC 5.3.1.1). Dihydroxyacetone phosphate as the substrate of the aforementioned reaction can be chemically or biochemically synthesized (refer to, for example, Itoh, N., Tsujibata, Y., Liu, J. Q., Appl. Microbiol. Biotechnol., volume 51, pp. 193-200, 1999).

However, the object of the aforementioned reports is academic analysis of the in vivo metabolism of pentose and the stereospecific action of aldolase, and the industrial production of glyceraldehyde 3-phosphate and 2-deoxyribose 5-phosphate is utterly beyond the scope of the reports. Up to now, a method of industrially producing 2-deoxyribose 5-phosphate has not been reported.

Regarding the preparation of 2-deoxyribose 5-phosphate by using an enzyme or an enzyme reagent, several examples have been reported in academic literatures as follows.

As one of these examples, there exists a report that 2-deoxyribose 5-phosphate was produced from glyceraldehyde 3-phosphate and acetaldehyde as the substrates, by the action of 2-deoxyribose-5-phosphate aldolase (Barbas, III, C. F., Wang, Y., Wong, C., J. Am. Chem. Soc., vol. 112, pp. 2013-2014, 1990). However, the production yield of 2-deoxyribose 5-phosphate with respect to the amount of the substrates as the raw materials cannot be known in this report, because the report does not disclose the amount of produced 2-deoxyribose 5-phosphate.

Further, as another example, there exists a report that 2-deoxyribose 5-phosphate was obtained from dihydroxyacetone phosphate and acetaldehyde as the substrates, by using a commercially available triose-phosphate isomerase as a biochemical reagent and a 2-deoxyribose-5-phosphate aldolase crude enzyme prepared from *Escherichia coli* which had been transformed with a plasmid having 2-deoxyribose-5-phosphate aldolase gene (deo C gene), in the presence of EDTA as a phosphatase inhibitor and nitrogen gas (Chen, L, Dumas, D. P., Wong, C., J. Am. Chem. Soc., vol. 114, pp. 741-748, 1992). However, in these academic reports, the enzymes are derived from different origins and purified at the level of a reagent. In addition, the influence of phosphatase cannot be completely eliminated, though a significant amount of EDTA is used in order to inhibit dephosphorylation by phosphatase. For this reason, the method is not suitable for industrial production of 2-deoxyribose 5-phosphate.

Glyceraldehyde 3-phosphate is an important intermediate in the saccharometabolism such as glycolytic pathway and pentose phosphate cycle (refer to, for example, page 411, the third edition, "Seikagaku Jiten (Dictionary of Biochemistry)", 1998, Tokyo Kagaku Dojin). Accordingly, glyceraldehyde 3-phosphate is metabolized to various courses by various enzymes in a cell. Also, there is a problem that the phosphate group of glyceraldehyde 3-phosphate tends to be easily cut off by phosphatase.

DISCLOSURE OF INVENTION

In consideration of the above-mentioned problems, the object of the present invention is to provide a method of preparing 2-deoxyribose 5-phosphate stably at a high yield. The first object of the present invention is to discover a microorganism containing a significant amount of an enzyme which is involved with the synthesis of 2-deoxyribose 5-phosphate but containing only an extremely small amount of unnecessary glycolytic enzymes such as phosphatase, so that 2-deoxyribose 5-phosphate can be obtained at a high yield, using glyceraldehyde 3-phosphate and acetaldehyde as the substrates, or dihydroxyacetone phosphate and acetaldehyde as the substrates.

In order to achieve the aforementioned object, the inventors of the present invention have made three steps of searches for the microorganism which fulfills the aforementioned conditions from a large number of and a variety of strains. As a result, the inventors have discovered the microorganism which produces 2-deoxyribose 5-phosphate at a high yield from either glyceraldehyde 3-phosphate and acetaldehyde or dihydroxyacetone phosphate and acetaldehyde as the substrates, thereby achieving the present invention.

The present invention is summarized as follows.

(1) A method of preparing 2-deoxyribose 5-phosphate, comprising:
reacting glyceraldehyde 3-phosphate and acetaldehyde, in the presence of either a microorganism itself which contains 2-deoxyribose-5-phosphate aldolase but substantially no phosphatase or the enzyme derived from the microorganism.

(2) A method of preparing 2-deoxyribose 5-phosphate, comprising:

reacting dihydroxyacetone phosphate and acetaldehyde, in the presence of either a microorganism itself which contains 2-deoxyribose-5-phosphate aldolase and triose-phosphate isomerase but substantially no phosphatase or the enzymes derived from the microorganism.

(3) A method of preparing 2-deoxyribose 5-phosphate according to the aforementioned (1), wherein said microorganism is a microorganism which belongs to Enterobacteriaceae.

(4) A method of preparing 2-deoxyribose 5-phosphate according to the aforementioned (2), wherein said microorganism is a microorganism which belongs to Enterobacteriaceae.

(5) A method of preparing 2-deoxyribose 5-phosphate, comprising:

reacting glyceraldehyde 3-phosphate and acetaldehyde, in the presence of either a microorganism itself which belongs to *Klebsiella* genus and contains 2-deoxyribose-5-phosphate aldolase or the enzyme derived from the microorganism.

(6) A method of preparing 2-deoxyribose 5-phosphate, comprising:

reacting dihydroxyacetone phosphate and acetaldehyde, in the presence of either a microorganism itself which belongs to *Klebsiella* genus and contains 2-deoxyribose-5-phosphate aldolase and triose-phosphate isomerase or the enzymes derived from the microorganism.

(7) A method of preparing 2-deoxyribose 5-phosphate according to any one of the aforementioned (1), (3) and (5), wherein said microorganism is *Klebsiella pneumoniae* B-44 (IFO 16579).

(8) A method of preparing 2-deoxyribose 5-phosphate according to any one of the aforementioned (2), (4) and (6), wherein said microorganism is *Klebsiella pneumoniae* B-44 (IFO 16579).

(9) *Klebsiella pneumoniae* B-44 (IFO 16579), which is capable of producing 2-deoxyribose-5-phosphate aldolase and triose-phosphate isomerase but substantially no phosphatase.

BRIEF DESCRIPTION OF DRAWINGS

FIG. 9 is a graph which shows the change with the passage of time, in the amount of 2-deoxyribose 5-phosphate produced from dihydroxyacetone phosphate in the optimum conditions.

BEST MODE FOR CARRYING OUT OF THE INVENTION

Figure 1:
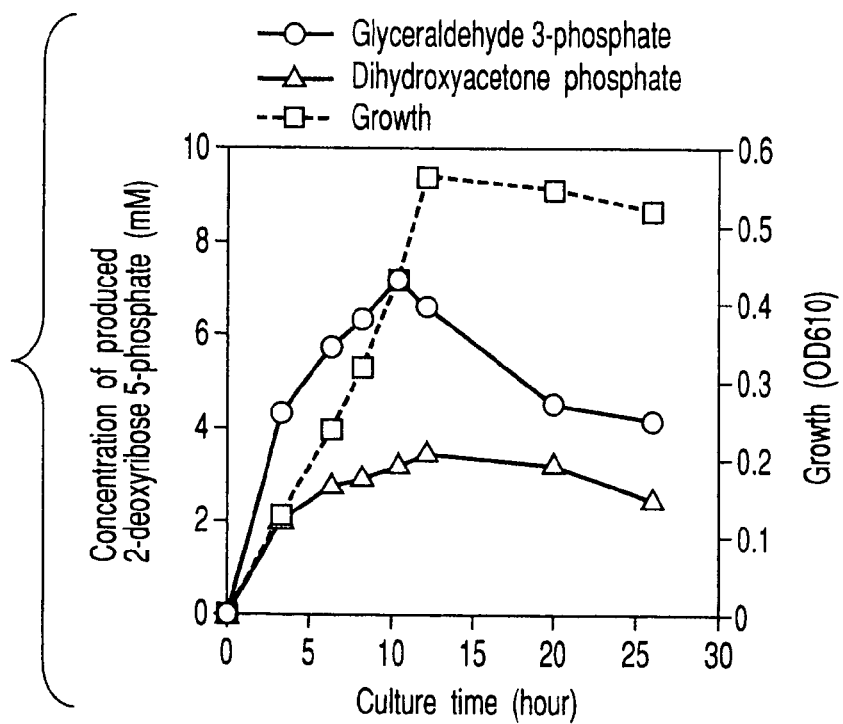
FIG. 1 is a graph which shows an effect of the culture time on the production of 2-deoxyribose 5-phosphate.

The present invention will be described in detail hereinafter.

{Synthesis of 2-deoxyribose 5-phosphate by an Enzyme Reaction}

In the method of the present invention, 2-deoxyribose 5-phosphate can be produced from glyceraldehyde 3-phosphate and acetaldehyde as the raw materials, by the catalytic action of a microorganism itself containing 2-deoxyribose-5-phosphate aldolase or by the catalytic action of the enzyme derived from the microorganism, as shown in the following formula (1). Hereinafter, 2-deoxyribose-5-phosphate aldolase will be also referred to as "DERA". The reaction of the formula (1) is an equilibrium reaction, but the equilibrium is biased toward the production side of 2-deoxyribose 5-phosphate.

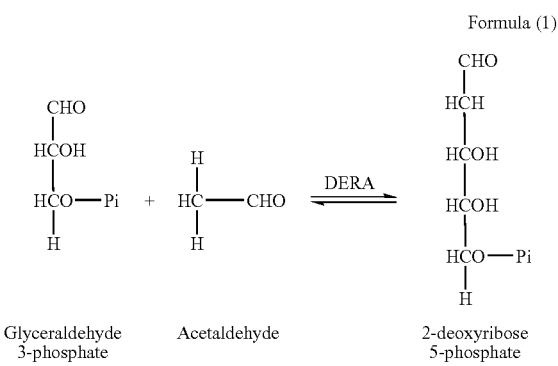

Formula (1)

Glyceraldehyde 3-phosphate + Acetaldehyde ⇌ 2-deoxyribose 5-phosphate

In the present invention, glyceraldehyde 3-phosphate can be produced by isomerizing dihydroxyacetone phosphate by the catalytic action of a microorganism itself containing triose-phosphate isomerase or by the catalytic action of the enzyme derived from the microorganism, as shown in the following formula (2). Hereinafter, triose-phosphate isomerase will be also referred to as "TPI".

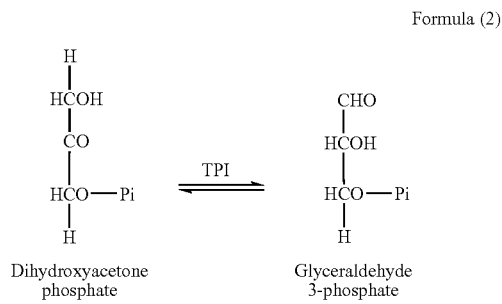

Formula (2)

Dihydroxyacetone phosphate ⇌ Glyceraldehyde 3-phosphate

When a microorganism contains both triose-phosphate isomerase and 2-deoxyribose-5-phosphate aldolase, the isomerization reaction of the formula (2) and the aldolase reaction of the formula (1) occur sequentially, as a result of the catalytic action of the microorganism itself or the enzymes derived from the microorganism. Therefore, in the present invention, 2-deoxyribose 5-phosphate can be produced from dihydroxyacetone phosphate and acetaldehyde as the raw materials, by the catalytic action of the aforementioned microorganism itself or the enzymes derived from the microorganism.

In the present invention, when the microorganism contains substantially no phosphatase, occurrence of unnecessary metabolism such as removal of the phosphate group by phosphatase can be prevented at the time of the reactions of the formulae (1) and (2). In this case, the actual value of the amount of produced 2-deoxyribose 5-phosphate is closer to the theoretical value, due to the prevention of unnecessary metabolism as described above.

{Raw Materials}

Acetaldehyde, glyceraldehyde 3-phosphate and dihydroxyacetone phosphate, used as the raw materials in the present invention, are all commercially available (refer to, for example, "1999 Catalog Handbook of Fine Chemicals" of Sigma Aldrich Japan co.,). Regarding the purity of the compounds used as the raw materials in the present invention, it suffices if the compounds are at least as pure as those generally used for industrial raw materials.

As glyceraldehyde 3-phosphate, DL-glyceraldehyde 3-phosphate can be used. However, D-glyceraldehyde 3-phosphate is more preferable.

Dihydroxyacetone phosphate may be obtained by synthesis, instead of using a commercial product. For example, dihydroxyacetone phosphate can be synthesized from dihydroxyacetone and phosphorus oxychloride used as industrial raw materials. Alternatively, dihydroxyacetone phosphate can be biochemically synthesized from dihydroxyacetone and acetyl phosphate as the raw materials by the catalytic action of dihydroxyacetone kinase (EC 2.7.1.29) (refer to, for example, Itoh, N., Tsujibata, Y., Liu, J. Q., Appl. Microbiol. Biotechnol., vol. 51, pp. 193-200, 1999).

{Microorganisms and Enzymes}

Deoxyribose-phosphate aldolase (DERA; EC 4.1.2.4) and triose-phosphate isomerase (TPI; EC 5.3.1.1) employed in the present invention may theoretically be derived from any type of microorganism. In the present invention, when glyceraldehyde 3-phosphate and acetaldehyde are used as the substrates, the type of the microorganism to be used is not particularly restricted as long as the microorganism contains DERA (here, it is acceptable that the microorganism also contains TPI). When dihydroxyacetone phosphate and acetaldehyde are used as the substrates, the type of the microorganism to be used is not particularly restricted as long as the microorganism contains DERA and TPI. In each case of using glyceraldehyde 3-phosphate and acetaldehyde or using dihydroxyacetone phosphate and acetaldehyde as the substrates, it is preferable that the microorganism contains substantially no phosphatase. In the present invention, the expression that "the microorganism contains substantially no phosphatase" means that the microorganism contains absolutely no phosphatase or, if any, the enzyme exhibits only a very weak activity which hardly affects the preparation method of the present invention.

In each case of using glyceraldehyde 3-phosphate/using dihydroxyacetone phosphate, preferable examples of the microorganism which satisfies the above-described condition include microorganisms which belong to Enterobacteriaceae. Specifically, these examples include microorganisms which belong to *Klebsiella* genus, *Enterobacter* genus or *Escherichia* genus. More specifically, preferable examples include *Klebsiella pneumoniae*, and more preferable examples include *Klebsiella pneumoniae* B-44 (IFO 16579) in each case.

The strain of *Klebsiella pneumoniae* B-44 was deposited at the Institute for Fermentation, Osaka (IFO; Feb. 17, 1985, Juso-honmachi, Yodogawa-ku, Osaka, 532-8686, JAPAN) on Mar. 1, 2001. The deposit number (accession number) thereof is IFO 16579. This "IFO strain" is available to any person, if desired.

The strain of *Klebsiella pneumoniae* B-44 is classified to Level 2 according to the biosafety level of microorganisms proposed by National Institute of Infectious Diseases (JAPAN). Due to this, National Institute of Advanced Industrial Science and Technology (JAPAN), whose previous appellation was National Institute of Bioscience and Human-Technology, Agency of Industrial Science and Technology, has refused to receive the strain, although AIST is an international deposit authority designated by the Budapest Treaty. This refusal has been officially admitted by AIST on Feb. 27, 2001.

In the present invention, the expression "reacting in the presence of a microorganism itself or an enzyme derived from the microorganism" means that reacting by using a suspension containing the microorganism (microorganism cell suspension) or using a solution containing enzyme produced by the microorganism. That is, in the present invention, the reaction may be performed by using the microorganism cell suspension or by collecting the enzyme produced by the microorganism and using it.

{Reaction Conditions, Separation and Purification of the Product, and Quantitative Determination of the Product}

Next, the reaction conditions in the reaction of producing 2-deoxyribose 5-phosphate will be described. The following reaction conditions are applied to both of the reaction in which glyceraldehyde 3-phosphate and acetaldehyde are used as the substrates and the reaction in which dihydroxyacetone phosphate and acetaldehyde are used as the substrates, unless described otherwise.

In the present invention, in both cases of using glyceraldehyde 3-phosphate and using dihydroxyacetone phosphate as a phosphate compound of the raw material, the initial concentration of the phosphate compound is preferably in a range of 5 to 500 mM, and more preferably in a range of 25 to 150 mM. The initial concentration of acetaldehyde is preferably in a range of 15 to 1000 mM, and more preferably in a range of 150 to 400 mM. The higher the concentration of acetaldehyde relative to the concentration of the phosphate compound as the substrate, the higher yield of 2-deoxyribose 5-phosphate per the consumed phosphate compound is expected.

The pH of the reaction solution is preferably in a range of 4.0 to 12.5, and more preferably in a range of 8.5 to 9.5. The temperature of the reaction solution is preferably in a range of 20 to 60° C., and more preferably in a range of 25 to 40° C. The reaction time may vary depending on the reaction conditions, but is normally in a range of 2 to 6 hours.

As the buffer solution to be used as the reaction solution, any buffer solution whose pH can be adjusted within the above-mentioned range or water can be employed. When glyceraldehyde 3-phosphate is used as the substrate, a 100-400 mM buffer solution (pH 8.5 to 9.5) is preferable. Specifically, a 200 mM Tris-hydrochloric acid buffer solution (pH 9.0) is more preferable in this case. When dihydroxyacetone phosphate is used as the substrate, water is preferably used as the buffer solution.

As the microorganism used in the reaction, a microorganism that is obtained by culturing a stock microorganism in a nutrient medium (e.g., DR culture medium) previously for 3 to 25 hours can be preferably used. More preferably, a microorganism that is obtained by culturing a stock microorganism in a nutrient medium previously for 8 to 20 hours can be used.

The cell concentration of the microorganism to be used in the reaction is preferably in a range of 1.0 to 20 weight %. The higher the cell concentration of the microorganism, the better result is achieved in the production of 2-deoxyribose 5-phosphate.

Produced 2-deoxyribose 5-phosphate can be collected from the reaction solution by ultrafiltration, ion exchange separation, adsorption chromatography and the like.

The quantity of the reaction product can be determined according to either of the following two methods. The first method is the Burton method (refer to, for example, pp. 664, the third edition, "Seikagaku Jiten (Dictionary of Biochemistry)", 1998, Tokyo Kagaku Dojin). This method sensitively detects 2-deoxyribose by the diphenylamine-acetic acid-sulfuric acid reaction, and thus achieves high specificity. The absorption coefficient of 2-deoxyribose 5-phosphate is equal to that of 2-deoxyribose.

The second method is an application of the cysteine-sulfate method, which is a colorimetry method of DNA (refer to, for example, Stumpf, P. K., J. Biol. Chem., vol. 169, pp. 367-371, 1947). In the present invention, 2-deoxyribose 5-phosphate was quantitatively measured by these methods.

{Culture Conditions and Preparation of the Enzyme}

The microorganism of the present invention is capable of growing well on a conventional culture medium for bacteria and producing the above-mentioned enzymes. It is more effective to add 2-deoxyribose, fructose, fructose-1,6-bisphosphate, dihydroxyacetone phosphate and the like, in amount of 0.1 to 2.0 weight %, to the culture medium, in terms of enhancing the enzyme activity.

As carbon and nitrogen sources for the microorganism of the present invention, yeast extract, meat extract, peptone or the like can be used. As the inorganic salt, ammonium chloride, potassium nitrate or the like can be used.

The microorganism that is cultured in the above-mentioned conditions can be used without being further treated, for the enzyme reaction in the present invention. Alternatively, the enzyme is obtained from the microorganism by a generally known method (e.g., disruption by using supersonication or milling, centrifugation, ammonium sulfate fractionation, membrane separation), and the resultant crude enzyme may also be used for the enzyme reaction.

{Bacteriological Characteristics}

The results of studying the bacteriological characteristics of the deposited strain according to "Bergey's Manual of Systematic Bacteriology, Volume 1 (1984)" and "Bergey's Manual of Determinative Bacteriology, the 9$^{th}$ edition (1994)" are as follows. The experiments were basically carried out by the method according to "Biseibutsu no Bunrui to Dotei (Classification and Determination of Microorganism)" by Takeji Hasegawa, revised edition, Gakkai Shuppan Center, 1985.

1. *Klebsiella pneumoniae* B-44 (IFO 16579) (which will be also referred to as "B-44 strain" hereinafter)
  1. Morphological characteristics
  (1) Shape and size of the cell: Rod, 0.8 μm×0.8-3.2 μm
  (2) Gram's stain: negative
  (3) Presence/Absence of polymorphism of the cell: absent
  (4) Motility: none
  (5) State of flagellum distribution: none
  (6) Presence/Absence of spore: none
  (7) Acid-fastness: none
  2. Characteristics in culture
  (1) Bouillon agar plate culture: circular, the peripheries are all smooth, slightly convexed, the surface layer is smooth, milky white with yellow tint.
  (2) Bouillon agar slant culture: milky white with yellow tint, opaque, spread allover the culture medium, good growth.
  (3) Bouillon liquid culture: moderately and evenly suspended, colorless.
  (4) Bouillon gelatin stab culture: no change
  (5) Litmus milk: slightly acidic, coagulated, generation of gas is observed.
  3. Physiological characteristics
  (1) Reduction of a nitrate: positive
  (2) Denitrification reaction: negative
  (3) MR test: positive
  (4) VP test: negative
  (5) Production of indole: negative
  (6) Production of hydrogen sulfide: negative
  (7) Hydrolysis of starch: negative
  (8) Utilization of citric acid
  Koser culture medium: positive
  Christensen culture medium: positive
  (9) Utilization of inorganic nitrogen source
  Nitrate: positive (weak)
  Ammonium salt: positive (weak)
  (10) Production of dye: negative
  (11) Urease: negative
  (12) Oxidase: negative
  (13) Catalase: positive
  (14) Range of growth
  pH: 3.5 to 10.2 (the optimum range is 5.0 to 8.0)
  Temperature range: 10 to 40° C. (the optimum range is 22 to 30° C.)
  (15) Reaction to oxygen: evenly grown, generation of gas is observed.
  (16) O—F test
  Glucose: F
  4. Other characteristics necessary for exhibiting the characteristics of the species
  (1) Utilization of various carbon sources
  Lactose: +
  Maltose: +
  D-xylose: +
  D-mannitol: +
  Raffinose: +
  D-sorbitol: +
  Sucrose: +
  Inositol: +
  Adonitol: +
  L-rhamnose: +
  L-arabinose: +
  D-mannose: +
  (2) β-galactosidase: +
  (3) Decarboxylation of arginine: −
  (4) Decarboxylation of lysine: +
  (5) Decarboxylation of ornithine: −
  (6) Hydrolysis of esculin: +
  (7) Utilization of organic acid
  Malonic acid: +
  Citric acid: +
  Gluconic acid: +
  n-capric acid: −
  Adipic acid: −
  DL-malic acid: +
  (8) Utilization of acetamide: −
  (9) Production of indole-pyruvic acid: −

(10) Arginine dehydrolase: −
(11) Hydrolysis of gelatin: −
(12) Capability of utilizing phenyl acetate as nutrition: −
5. Chemotaxonomical characteristics
(1) GC content: 50 to 52 mol % (HPLC method)
Judging from the aforementioned bacteriological characteristics, the present strain can be determined to be *Klebsiella pneumoniae*.

EXAMPLES

The present invention will be described in more detail by the following Experiment examples and Examples.

In the Experiment examples and Examples, 2-deoxyribose and 2-deoxyribose 5-phosphate were both analyzed according to TLC, the Burton method and the cysteine-sulfate method described below. Standard compounds were added to DR culture medium (as described in Experiment example 3 described below), and the identification and quantitative determination were carried out according to the Burton method and the cysteine-sulfate method. The result showed that the value obtained by the quantitative determination was the same as the weighed amount.

(1) Detection and Identification of Sugars by Thin Layer Chromatography (TLC)

Standard compounds of 2-deoxyribose 5-phosphate, 2-deoxyribose, acetaldehyde, glyceraldehyde 3-phosphate and dihydroxyacetone phosphate, and samples were spotted on a plate for thin layer chromatography (Kieselgel 60F254, manufactured by Merck co.,). It was developed using a mixture of n-butanol, acetic acid and water=3:1:1 (v/v/v) as a developer. Thereafter, p-anisaldehyde-sulfuric acid, which had been prepared by dissolving 0.5 mL of p-anisaldehyde in 50 mL of acetic acid and adding 1 mL of concentrated sulfuric acid thereto, was sprayed on the plate, and the plate was heated. The detection and identification of the product was carried out on the basis of the Rf value and the exhibited color thereof.

(2) Quantitative Determination of 2-deoxyribose 5-phosphate by the Burton Method 1.5 g of diphenylamine was dissolved in 100 mL of redistilled glacial acetic acid containing 1.5 mL of concentrated sulfuric acid. To 20 mL of the solution, 0.1 mL of acetaldehyde aqueous solution (16 mg/mL) was added, thereby preparing a reagent. 2 mL of the reagent was added to 1 mL of a sample containing 5 to 100 μg of 2-deoxyribose. The resultant mixture was left still for 16 to 20 hours at 30° C., and then absorbance at 600 nm was measured. The scale was reduced appropriately. The measured value can be regarded as the amount of produced 2-deoxyribose 5-phosphate, unless 2-deoxyribose is detected by TLC.

(3) Quantitative Determination of 2-deoxyribose 5-phosphate by the cysteine-sulfate Method A standard sample solution containing 5 to 100 μg of 2-deoxyribose 5-phosphate was prepared in advance. 17.5 μL of 5% (w/v) cysteine-hydrochloric acid solution was added to 17.5 μL of the standard sample solution. 175 μL of 70% sulfuric acid was further added. The resultant mixture was stirred quickly, left still for 10 minutes at the room temperature (25° C.), and then the absorbance at 490 nm was measured.

Experiment Example 1

First Screening on the Basis of the Capability of Degrading 2-deoxyribose 700 strains of bacteria, 100 strains of actinomycetes, 100 strains of molds, 100 strains of basidiomycetes, and 500 strains of soil bacteria which are capable of utilizing 2-deoxyribose as nutrition, were cultured by the conventional shaking culture or stationary culture, whereby wet-cells of each type of microorganisms were obtained. The wet-cells of each type of microorganisms were added to a phosphate buffer solution (100 mM, pH 7.0) containing 2-deoxyribose (20 mM), and it was shaken for 1 or 2 days at 28° C. The resultant solution was filtered, and a predetermined amount of the filtrate was spotted on a TLC plate. Thereby the capability of degrading 2-deoxyribose was analyzed. The result is shown in Table 1.

TABLE 1

| Type of microorganism | Number of strain used | Number of strain capable of degrading 2-deoxyribose |
|---|---|---|
| Bacteria | 700 | 8 |
| Actinomycetes | 100 | 3 |
| Molds | 100 | 0 |
| Basidiomycetes | 100 | 3 |
| Soil bacteria | 500 | 68 |

Experiment Example 2

Second Screening on the Basis of the Capability of Producing Acetaldehyde from 2-deoxyribose by the Action of the Cell Extract Solution Each strain whose capability of degrading 2-deoxyribose had been confirmed in Experiment example 1 was cultured by the conventional method. The cells of each cultured strain were disrupted by supersonication and centrifuged, and thereby supernatant was obtained. 20 μL of 100 mM Tris-hydrochloric acid buffer solution (pH 8.8), 10 μL of 0.5 mM NADH (reduced nicotinamide adenine dinucleotide), 30 U of alcohol dehydrogenase (manufactured by Sigma Aldrich Japan co., "1U" indicates an enzyme activity whereby 1.0 μmol of ethanol is completely converted into aldehyde for 1 minute at pH 8.8 at 25° C.), and 10 μL of either 2-deoxyribose 5-phosphate or 2-deoxyribose were added to 20 μL of the obtained supernatant. The resultant solution was left still at 30° C. The change in absorbance at 340 nm with the passage of time was measured.

$$C_2H_5OH + NAD^+ \rightleftharpoons CH_3CHO + NADH + H^+$$

In the measurement, the amount of acetaldehyde which has been produced as a result of degradation of 2-deoxyribose 5-phosphate or 2-deoxyribose by the action of 2-deoxyribose-5-phosphate aldolase is determined, by estimating, based on the change in absorbance at 340 nm, the decrease in NADH caused by the reduction of acetaldehyde to ethanol.

The activity of 2-deoxyribose-5-phosphate aldolase of each strain, which has been estimated from the amount of produced acetaldehyde, is shown in Table 2. In Table 2, "−" indicates that no enzyme activity has been detected, and "+" indicates that at least some enzyme activity has been detected. The larger number of "+" indicates the higher enzyme activity.

TABLE 2

| Type of microorganism | Number of strain | Substrate | |
|---|---|---|---|
| | | 2-deoxyribose 5-phosphate | 2-deoxyribose |
| Bacteria | 7 | + | − |
| Bacteria | 1 | ++ | − |
| Actinomycetes | 3 | + | − |
| Basidiomycetes | 3 | ++ | − |
| Soil bacteria | 8 | ++++ | − |
| Soil bacteria | 13 | +++ | − |
| Soil Bacteria | 47 | ++ | − |

Experiment Example 3

Selection of Culture Medium for Culturing the Microorganism

The 8 strains of the soil bacteria, which had exhibited high enzyme activity in Experiment example 2, were transferred to each type of the culture medium described below. Each sample was subjected to shaking culture overnight at 28° C., whereby wet-cells of each bacterium was obtained. For each sample, the activity of degrading 2-deoxyribose 5-phosphate was measured in a manner similar to that of Experiment example 2. The result showed that the enzyme activity is generally increased by twice or several times in the DR culture medium, as compared with the enzyme activity observed in the other two types of the culture medium. Similarly in a case of adding, to the DR culture medium, fructose, fructose-1,6-bisphosphate, dihydroxyacetone phosphate or the like, instead of 2-deoxyribose, the enzyme activity was enhanced, although the enhancing effect was not so excellent as that of 2-deoxyribose.

(Culture Medium)

(1) NB culture medium: Nutrient broth (manufactured by DIFCO co.,) to which 0.1% yeast extract had been added (2) TGY culture medium: 0.5% Tryptone (manufactured by DIFCO co.,), 0.5% yeast extract, 0.1% glucose, and 0.1% dipotassium hydrogenphosphate (pH 7.0)

(3) DR culture medium: 0.5% 2-deoxyribose, 0.2% ammonium chloride, 0.1% potassium dihydrogenphosphate, 0.1% dipotassium hydrogenphosphate, 0.03% magnesium sulfate-.heptahydrate, and 0.01% yeast extract (pH 7.0).

Experiment Example 4

Third Screening on the Basis of the Capacity of Producing 2-deoxyribose 5-phosphate from acetaldehyde and glyceraldehyde 3-phosphate The enzyme activity of synthesizing 2-deoxyribose 5-phosphate was measured, in the following conditions, in the 8 strains of the soil bacteria which had exhibited high enzyme activity of deoxyribose-phosphate aldolase in Experiment example 2. As a result, 2-deoxyribose 5-phosphate was detected, but 2-deoxyribose was not detected. From the measured values, it turned out that the B-44 strain was the most excellent strain. It also turned out that a larger amount of 2-deoxyribose 5-phosphate was produced at pH 8.5 than at pH 7.0.

(Preparation of Wet-cells)

5 mL of DR culture medium was filled in a test tube (16×165 mm), and a platinum loop of the soil bacteria strain was inoculated into the culture medium. The inoculated strain was subjected to shaking culture (300 rpm) for 2 days at 28° C. The resultant cultured solution was transferred to a 2 L Erlenmeyer flask containing 500 mL of DR culture medium, and further subjected to shaking culture (120 rpm) for 2 days at 28° C. The resultant cultured solution was centrifuged at 8000 rpm. The precipitate was washed with 0.85% (w/v) saline solution twice, whereby wet-cells were obtained.

(Reaction Conditions)

20% (w/v) of the above-described wet-cells were added to 60 μL of an aqueous solution, which had been prepared so as to contain 166 mM Tris-hydrochloric acid buffer solution (pH 8.5) or 166 mM phosphate buffer solution (pH 7.0), 333 mM acetaldehyde and 100 mM DL-glyceraldehyde 3-phosphate. The mixture was stirred at 30° C. for 3 hours and then centrifuged, whereby supernatant was obtained. The amount of produced 2-deoxyribose 5-phosphate in the supernatant was determined.

Example 1

The Substrate which can be Utilized by the Enzyme System of the B-44 Strain for Producing 2-deoxyribose-5-phosphate Each of Nos. 1 to 12 substrates listed in Table 3 was added, together with 333 mM acetaldehyde, to any one of 150 mM acetic acid-sodium acetate buffer solution (pH 5.5), 150 mM phosphate buffer solution (pH 7.0), and 166 mM Tris-hydrochloric acid buffer solution (pH 8.5). 20% (w/v) of the wet-cells of the B-44 strain (which had been subjected to shaking culture at 28° C. overnight in DR culture medium described in Experiment example 3) were added to each of the prepared solutions containing each substrate. Each mixture was stirred at 30° C. for 3 hours and then centrifuged, whereby supernatant was obtained. The amount of produced 2-deoxyribose 5-phosphate in the supernatant was determined.

The results are shown in Table 3. It has been demonstrated that 2-deoxyribose 5-phosphate was produced advantageously on the basic side and that DL-glyceraldehyde 3-phosphate and dihydroxyacetone phosphate were excellent as the substrates. In Table 3, "−" indicates that the amount of produced 2-deoxyribose 5-phosphate was zero or hardly traceable, and "+" indicates that production of 2-deoxyribose 5-phosphate was confirmed. The larger number of "+" indicates the larger amount of produced 2-deoxyribose 5-phosphate.

TABLE 3

| Sample | | 2-deoxyribose 5-phosphate | | |
|---|---|---|---|---|
| No. | Substrate | pH 5.5 | pH 7.0 | pH 8.5 |
| 1 | DL-glyceraldehyde 3-phosphate (100 mM) | + | ++ | +++ |
| 2 | DL-glyceraldehyde (166 mM) | − | − | + |
| 3 | Glycerophosphoric acid (100 mM) | − | − | − |
| 4 | Glycerol (100 mM) | − | − | − |
| 5 | Dihydroxyacetone phosphate (33 mM) | + | ++ | +++ |
| 6 | Dihydroxyacetone (166 mM) | − | − | + |
| 7 | Fructose 1,6-bisphosphate (166 mM) | − | − | + |
| 8 | Fructose 6-phosphate (166 mM) | − | − | − |
| 9 | Fructose (100 mM) | − | − | − |
| 10 | Glucose 1,6-bisphosphate (100 mM) | − | − | − |
| 11 | Glucose 6-phosphate (100 mM) | − | − | − |
| 12 | Glucose (100 mM) | − | − | − |

Example 2

Optimum Culture Time of Microorganism

The B-44 strain was cultured in the following conditions, and the wet-cells were collected periodically. The bacterial capability of producing 2-deoxyribose 5-phosphate was evaluated.

The results are shown in FIG. 1. In both cases of using glyceraldehyde 3-phosphate and using dihydroxyacetone phosphate as the substrate, the cells which had been culture for 10 to 12 hours exhibited the highest activity. Therefore, the wet-cells which had been cultured for 10 to 12 hours were employed in all of the subsequent examples. In FIG. 1, "-O-" represents the concentration (mM) of produced 2-deoxyribose 5-phosphate when glyceraldehyde 3-phosphate was used as the substrate. "-Δ-" represents the concentration (mM) of produced 2-deoxyribose 5-phosphate when dihydroxyacetone phosphate was used as the substrate. "-□-" represents the degree of growth (the degree of turbidity) of the B-44 strain. Similarly, the symbols of "-O-" and "-Δ-" employed in FIGS. 2 to 9 represent the same meaning as in FIG. 1.

(Culture Conditions and Preparation of Wet-cells)

5 mL of DR culture medium was filled in a test tube (16×165 mm), and a platinum loop of the B-44 strain was inoculated into the culture medium. The inoculated B-44 strain was subjected to shaking culture (300 rpm) for 2 days at 28° C. The resultant cultured solution was transferred to a 2 L Erlenmeyer flask containing 500 mL of DR culture medium, and further subjected to shaking culture (120 rpm) at 28° C. The cultured solution was periodically collected and centrifuged at 8000 rpm. The precipitate was washed with 0.85% (w/v) saline solution twice, whereby wet-cells were obtained. In order to know the degree of growth of the B-44 strain from the degree of turbidity, the relationship between the amount of the wet-cells and the degree of turbidity was analyzed, and a formula for conversion was prepared previously.

(Reaction Conditions)

(1) In a case of using glyceraldehyde 3-phosphate as the substrate

Glyceraldehyde 3-phosphate: 87.5 mM
Acetaldehyde: 200 mM
Tris-hydrochloric acid buffer solution: 200 mM, pH 9.0
Wet-cells: 12.5% (w/v)
Reaction: shaking at 30° C. for 3 hours (2) In a case of using dihydroxyacetone phosphate as the substrate Dihydroxyacetone phosphate: 116.6 mM
Acetaldehyde: 200 mM
Tris-hydrochloric acid buffer solution: 200 mM, pH 9.0
Wet-cells: 16.6% (w/v)
Reaction: shaking at 30° C. for 3 hours (Method of Quantitative Determination)

After the reaction was completed, the reaction solution was immediately centrifuged, and supernatant was obtained. The amount of produced 2-deoxyribose 5-phosphate in the supernatant was determined.

Example 3

Optimum pH in the Reaction

Figure 2:
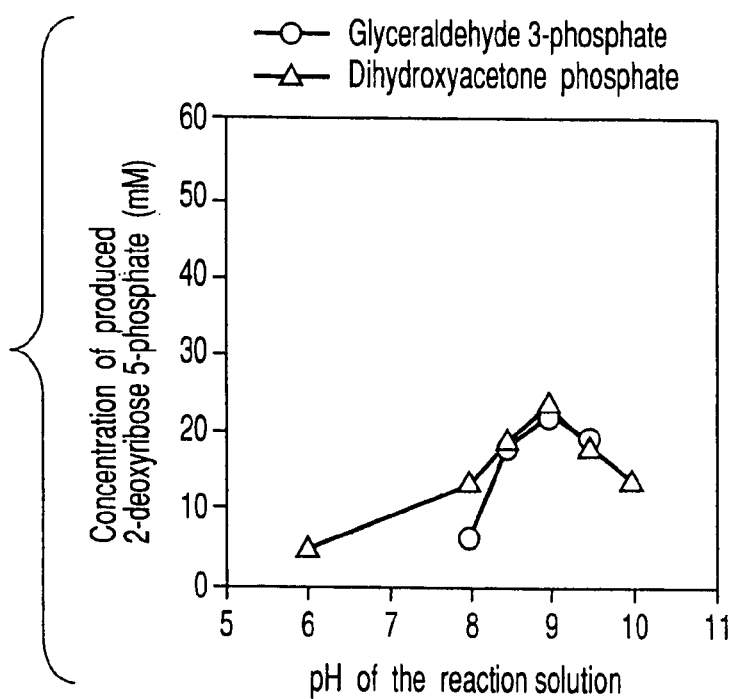
FIG. 2 is a graph which shows an effect of pH of the reaction solution on the production of 2-deoxyribose 5-phosphate.

The optimum pH of the reaction solution was investigated by using wet-cells which had been cultured for 10 to 12 hours. The reaction conditions were basically the same as those of Example 2, except that the pH value of the reaction solution was varied from pH 6.0 to 8.5 by using 150 mM phosphate buffer solution and from pH 7.5 to 10.0 by using 150 mM Tris-hydrochloric acid buffer solution. The results are shown in FIG. 2. The optimum pH was 9.0 in both cases of using glyceraldehyde 3-phosphate and using dihydroxyacetone phosphate as the substrate.

Example 4

Optimum Concentration of the Buffer Solution for the Reaction

Figure 3:
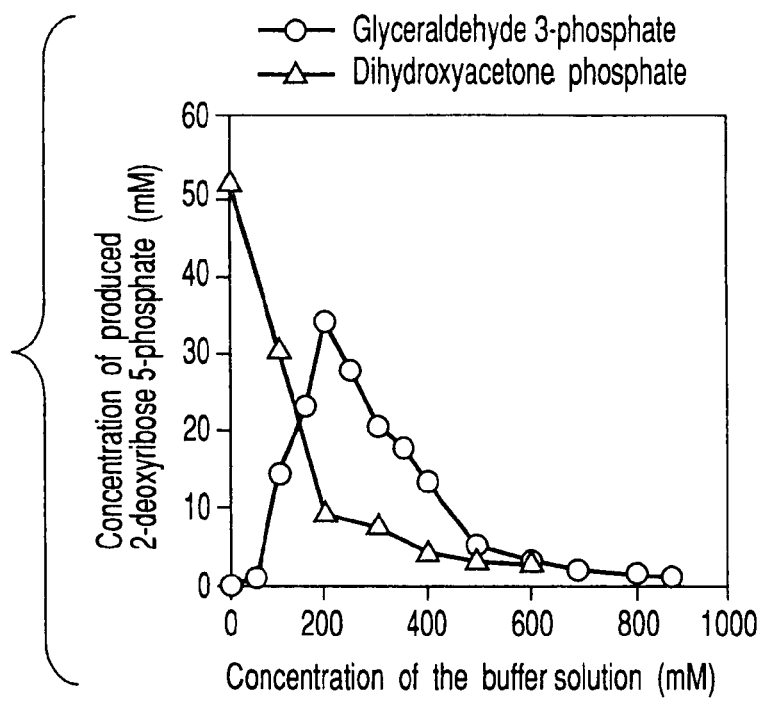
FIG. 3 is a graph which shows an effect of concentration of the Tris-hydrochloric acid buffer solution (pH 9.0) on the production of 2-deoxyribose 5-phosphate.

The optimum concentration of the buffer solution for the reaction was investigated by using wet-cells which had been cultured for 10 to 12 hours. The reaction conditions were basically the same as those of Example 2, except that the concentration of Tris-hydrochloric acid buffer solution of pH 9.0 was varied in a range of 0 to 900 mM. The results are shown in FIG. 3. When glyceraldehyde 3-phosphate was used as the substrate, the activity exhibited the highest value in the case of the concentration of the buffer solution of 200 mM. On the other hand, when dihydroxyacetone phosphate was used as the substrate, the lower the concentration of the buffer solution was, the higher activity was achieved. In this case, the activity reached the highest level, when no buffer solution (i.e., only water) was used.

Example 5

Optimum Cell Concentration in the Reaction Solution

Figure 4:
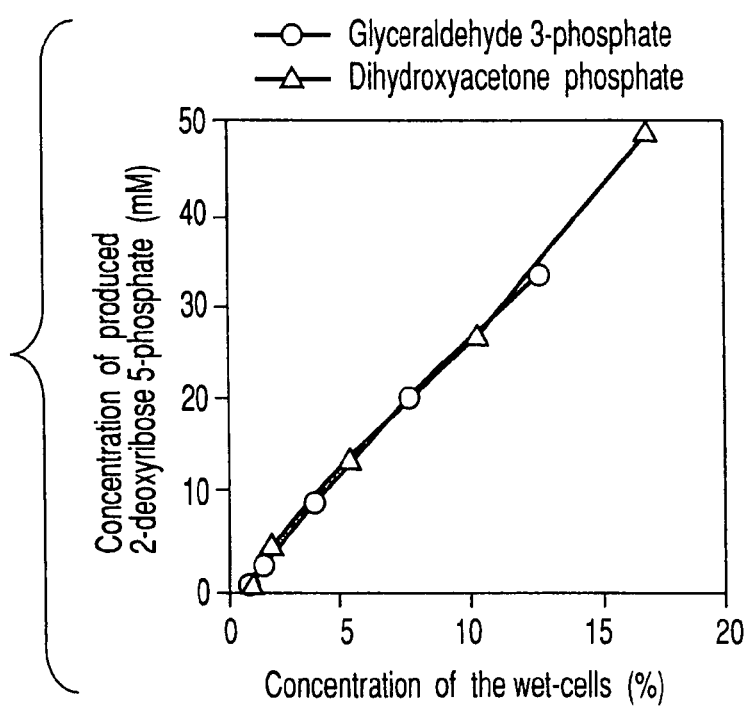
FIG. 4 is a graph which shows an effect of concentration of the microorganism cells in the reaction solution on the production of 2-deoxyribose 5-phosphate.

The optimum cell concentration in the reaction solution was investigated by using wet-cells which had been cultured for 10 to 12 hours. The reaction conditions were basically the same as those of Example 2, except that water was used as the reaction solution when dihydroxyacetone phosphate was used as the substrate. The results are shown in FIG. 4. In both cases of using glyceraldehyde 3-phosphate and using dihydroxyacetone phosphate as the substrate, the higher the cell concentration is, the larger amount of 2-deoxyribose 5-phosphate was produced in the investigated range of the cell concentration (i.e., 0.75 to 16.6% (w/v)). A generally linear, proportional relationship was observed between the cell concentration and the amount of produced 2-deoxyribose 5-phosphate in the investigated range of the cell concentration.

Example 6

Optimum Concentration of Acetaldehyde in the Reaction Solution

Figure 5:
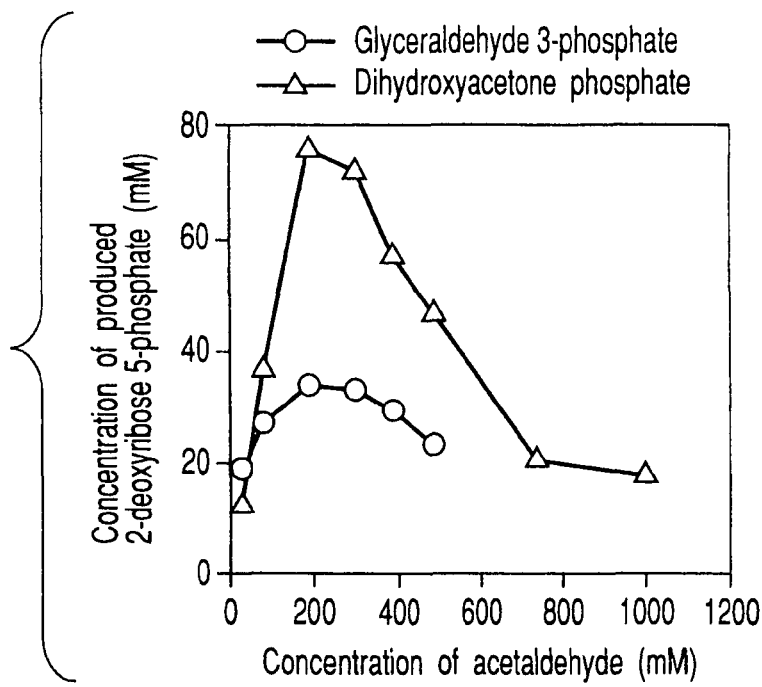
FIG. 5 is a graph which shows an effect of concentration of acetaldehyde in the reaction solution on the production of 2-deoxyribose 5-phosphate.

The optimum concentration of acetaldehyde in the reaction solution was investigated by using wet-cells which had been cultured for 10 to 12 hours. The reaction conditions were basically the same as those of Example 2, except that the concentration of acetaldehyde was varied in a range of 0 to 1000 mM and that water was used instead of the buffer solution when dihydroxyacetone phosphate was used as the substrate. The results are shown in FIG. 5. In both cases of using 87.5 mM of glyceraldehyde 3-phosphate and using 116.6 mM of dihydroxyacetone phosphate as the substrate, the optimum concentration of acetaldehyde was 200 mM.

Example 7

Optimum Concentration of the Substrate

The optimum concentration of the substrate in the reaction solution was investigated by using wet-cells which had been cultured for 10 to 12 hours. The reaction conditions were basically the same as those of Example 2, except that the concentrations of glyceraldehyde 3-phosphate and dihydroxyacetone phosphate as the substrate were each varied within a range of 0 to 125 mM and that water was used instead of the buffer solution when dihydroxyacetone phosphate was used as the substrate.

Figure 6:
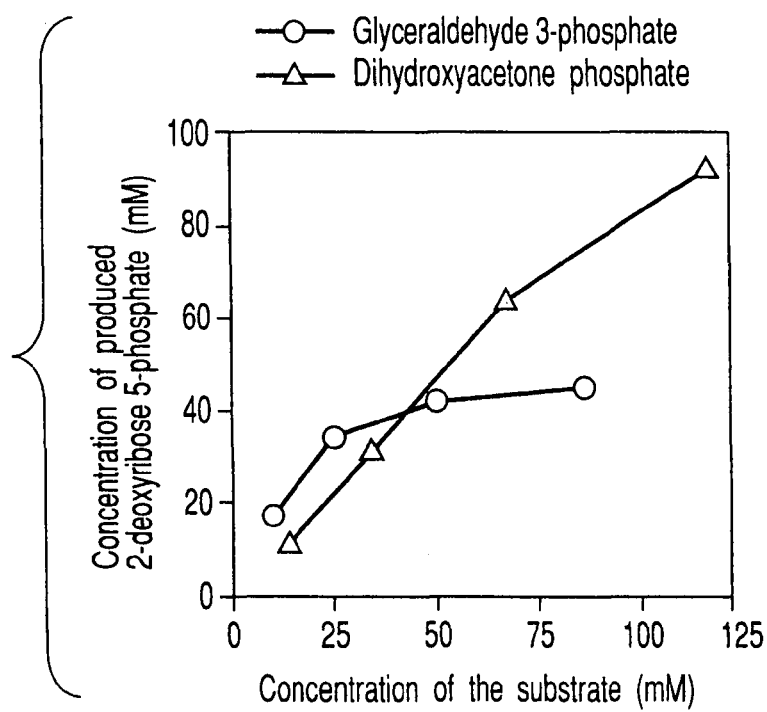
FIG. 6 is a graph which shows an effect of concentration of the substrate in the reaction solution on the production of 2-deoxyribose 5-phosphate, in each case of using glyceraldehyde 3-phosphate and dihydroxyacetone phosphate as the substrate.

The results are shown in FIG. 6. In both glyceraldehyde 3-phosphate and dihydroxyacetone phosphate, in the presence of 200 mM acetaldehyde, the higher the concentration of the substrate was, the larger amount of 2-deoxyribose 5-phosphate was produced. In the case of using dihydroxyacetone phosphate as the substrate, the amount of produced 2-deoxyribose 5-phosphate increased almost linearly, i.e., generally proportional to the increase in concentration of the substrate, in the investigated concentration range of the substrate. However, in the case of using glyceraldehyde 3-phosphate as the substrate, the amount of produced 2-deoxyribose 5-phosphate substantially reached a plateau in the concentration range of the substrate of 25 mM or higher.

Example 8

Optimum Reaction Temperature

Figure 7:
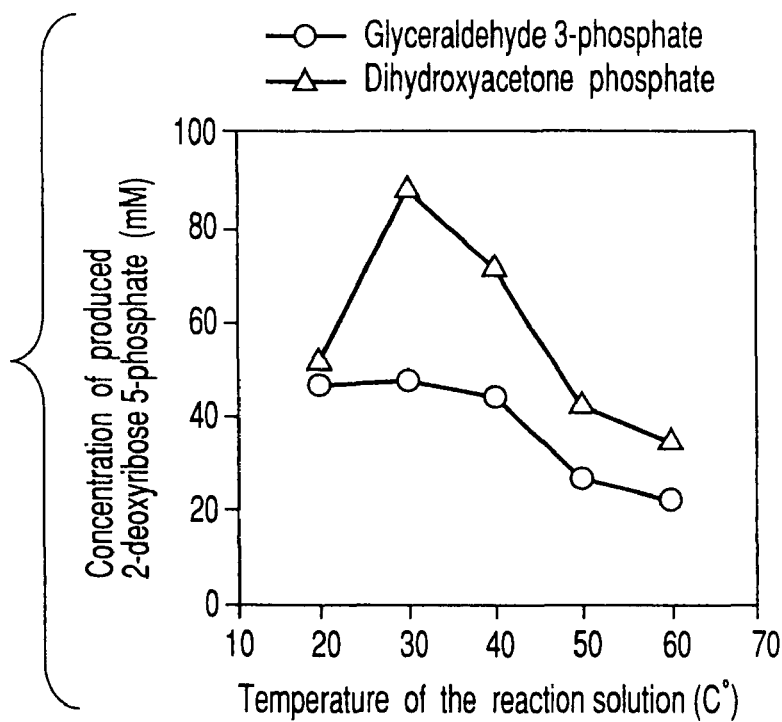
FIG. 7 is a graph which shows an effect of temperature of the reaction solution on the production of 2-deoxyribose 5-phosphate.

The optimum temperature of the reaction solution was investigated by using wet-cells which had been cultured for 10 to 12 hours. The reaction conditions were basically the same as those of Example 2, except that the temperature was varied and that water was used instead of the buffer solution when dihydroxyacetone phosphate was used as the substrate. The results are shown in FIG. 7. In both cases of using glyceraldehyde 3-phosphate and using dihydroxyacetone phosphate as the substrate, the optimum temperature was 30° C.

Example 9

Figure 8:
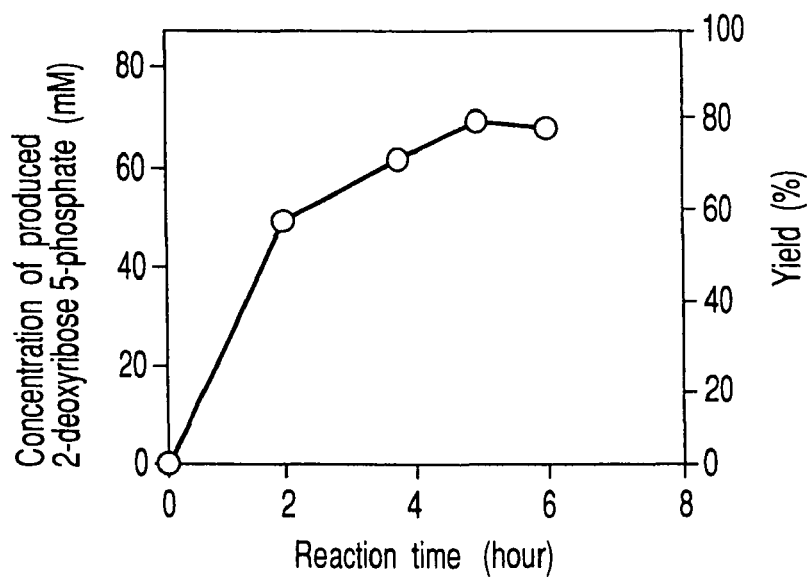
FIG. 8 is a graph which shows the change with the passage of time, in the amount of 2-deoxyribose 5-phosphate produced from glyceraldehyde 3-phosphate in the optimum conditions.

Change with the Passage of Time, in the Amount of Produced 2-deoxyribose 5-phosphate from glyceraldehyde 3-phosphate in the Optimum Conditions On the basis of the result obtained by the aforementioned examples, the change with the passage of time in the amount of produced 2-deoxyribose 5-phosphate from glyceraldehyde 3-phosphate in the optimum conditions was observed. The results are shown in FIG. 8. The highest yield of 2-deoxyribose 5-phosphate was obtained five hours after the start of the reaction. Specifically, 70.8 mM of 2-deoxyribose 5-phosphate was obtained from 200 mM of acetaldehyde and 87.5 mM of glyceraldehyde 3-phosphate. The yield of 2-deoxyribose 5-phosphate with respect to the consumed glyceraldehyde 3-phosphate was 80.9%.

(Culture Conditions and Preparation of Wet-cells)

5 mL of DR culture medium was filled in a test tube (16×165 mm), and a platinum loop of the B-44 strain was inoculated into the culture medium. The inoculated B-44 strain was subjected to shaking culture (300 rpm) for 2 days at 28° C. The resultant cultured solution was transferred to a 2 L Erlenmeyer flask containing 500 mL of DR culture medium, and further subjected to shaking culture (120 rpm) for 10 to 12 hours at 28° C. Thereafter, the resultant strain was washed with 0.85% (w/v) saline solution twice, whereby wet-cells were obtained.

(Reaction Conditions)
Glyceraldehyde 3-phosphate: 87.5 mM
Acetaldehyde: 200 mM
Tris-hydrochloric acid buffer solution: 200 mM, pH 9.0
Wet-cells: 12.5% (w/v)
Reaction: shaking at 30° C. for 3 hours Example 10

Change with the Passage of Time, in the Amount of Produced 2-deoxyribose 5-phosphate from dihydroxyacetone phosphate in the Optimum Conditions On the basis of the result obtained by the aforementioned examples, the change with the passage of time in the amount of produced 2-deoxyribose 5-phosphate from dihydroxyacetone phosphate in the optimum conditions was observed. The results are shown in FIG. 9. The highest yield of 2-deoxyribose 5-phosphate was obtained five hours after the start of the reaction. Specifically, 98.7 mM of 2-deoxyribose 5-phosphate was obtained from 200 mM of acetaldehyde and 116.6 mM of dihydroxyacetone phosphate. The yield of 2-deoxyribose 5-phosphate with respect to the consumed dihydroxyacetone phosphate was 84.6%.

(Culture Conditions and Preparation of Wet-cells)

5 mL of DR culture medium was filled in a test tube (16×165 mm), and a platinum loop of the B-44 strain was inoculated into the culture medium. The inoculated B-44 strain was subjected to shaking culture (300 rpm) for 2 days at 28° C. The resultant cultured solution was transferred to a 2 L Erlenmeyer flask containing 500 mL of DR culture medium, and further subjected to shaking culture (120 rpm) for 10 to 12 hours at 28° C. Thereafter, the resultant strain was washed with 0.85% (w/v) saline solution twice, whereby wet-cells were obtained.

(Reaction Conditions)
Dihydroxyacetone phosphate: 116.6 mM
Acetaldehyde: 200 mM
Aqueous solution: Distilled water was used instead of a buffer solution.
Wet-cells: 16.6% (w/v)
Reaction: shaking at 30° C. for 3 hours {Advantageous Effect of the Present Invention}

According to the present invention, 2-deoxyribose 5-phosphate can be produced stably at a high yield, by using the enzyme reaction of microorganism, from glyceraldehyde 3-phosphate and acetaldehyde as the starting materials. Similarly, according to the present invention, 2-deoxyribose 5-phosphate can be produced stably at a high yield, by using the enzyme reaction of microorganism, from dihydroxyacetone phosphate and acetaldehyde as the starting materials.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of preparing 2-deoxyribose 5-phosphate, comprising:
reacting dihydroxyacetone phosphate and acetaldehyde, in the presence of *Klebsiella pneumoniae* B-44 (IFO 16579) which contains 2-deoxyribose-5-phosphate aldolase and triose-phosphate isomerase.

2. The method preparing 2-deoxyribose 5-phosphate according to claim 1, wherein said dihydroxyacetone phosphate has a concentration of 25 to 150 mM and said acetaldehyde has a concentration of 150 to 400 mM.

3. The method preparing 2-deoxyribose 5-phosphate according to claim 1, wherein said reaction of dihydroxyacetone phosphate and acetaldehyde is carried out in water.

4. The method preparing 2-deoxyribose 5-phosphate according to claim 1, wherein said reaction of dihydroxyacetone phosphate and acetaldehyde is carried out at a temperature of 25 to 40° C. for a duration of 2 to 6 hours.

5. The method preparing 2-deoxyribose 5-phosphate according to claim 1, wherein said *Klebsiella pneumoniae* B-44 (IFO 16579 is prepared by previously culturing a stock microorganism thereof in a nutrient medium for 8 to 20 hours.

* * * * *